United States Patent
Borsodi et al.

Patent Number: 5,457,110
Date of Patent: Oct. 10, 1995

[54] APIOID ANALGESIC WITHOUT RESPIRATORY DEPRESSION

[75] Inventors: Anna Borsodi, Szeged Vitéz utca; Zsuzsa Fürst, Budapest Toldy; Sándor Hosztafi, Monostorpály Arpád; Schäfferné E. Varga, Szeged Föfasor; Beáta Buzás, Eger Maklári; Tamás Friedmann, Budapest Budekeszi; Sandor Benyhe; Mária Szücs, both of Szeged József A. sugárút, all of Hungary

[73] Assignee: Alkaloida Chemical Company, Ltd., Tiszavasvari, Finland

[21] Appl. No.: 246,364

[22] Filed: May 19, 1994

Related U.S. Application Data

[63] Continuation of Ser. No. 934,547, Oct. 2, 1992, Pat. No. 5,317,022.

[30] Foreign Application Priority Data

Feb. 4, 1991 [HU] Hungary .................................. 369/91

[51] Int. Cl.$^6$ .................................................. A61K 31/485
[52] U.S. Cl. ................................................................ 514/282
[58] Field of Search ............................................... 514/282

[56] References Cited

U.S. PATENT DOCUMENTS

| | | | |
|---|---|---|---|
| 4,760,069 | 7/1988 | Otarski et al. | 514/282 |
| 4,889,860 | 12/1989 | Otarski et al. | 514/282 |
| 5,232,926 | 8/1993 | Hoaztaff et al. | 514/282 |

FOREIGN PATENT DOCUMENTS

| | | |
|---|---|---|
| 0077521 | 4/1983 | European Pat. Off. . |
| 0242417 | 10/1987 | European Pat. Off. . |

OTHER PUBLICATIONS

Receptor Binding and Analgesic Properties of Oxymorphazone, S. Galleta, et al., Life Sciences, (1983) vol. 31, pp. 1389–1392.
Long–Acting Opiate Agonists and Antagonists, G. W. Pasternak, Journal of Medicinal Chemistry (1980) vol. 23, No. 6, pp. 674–676.
Classification of Apioid Receptors, S. J. Peterson, et al. British Medical Bulletin (1983), vol. 39, No. 1, pp. 31–36.
Prolonged Receptor Blockade by Opioid Receptor Probes, A. Koman, et al., Pharmaceutical Research (1986) vol. 3, No. 1, pp. 56–60.
Synthesis and Binding of hu 3H–Oxymorphazone to Rat Brain Membranes, E. Varga, et al., Life Sciences, vol. 40, pp. 1579–1588 (1987).
The Case for Multiple Opiate Receptors receptors R. S. Zukin, et al., TINS, May 19, 1984, pp. 160–164.
Opiate and Analgesia: Evidence for Mediation by a Subpopulation of Opiate Receptors, Science (1980) vol. 208, pp. 514–516.
Classification of Opioid Receptors, S. J. Peterson, et al. British Medical Bulletin (1983) vol. 39, No. 1 pp. 31–36.
Naloxazone, a Long–Acting Opiate Antagonist: Effects on Analgesia in Intact Animals and on Opiate Receptor Bkinding in Vitro, G. W. Pasternak, et al., Journal of Pharmacology and Exper. Therap. (1980) vol. 214, No. 3, pp. 455–462.

*Primary Examiner*—Raymond Henley, III
*Assistant Examiner*—Keith MacMillan
*Attorney, Agent, or Firm*—Steinberg, Raskin & Davidson

[57] ABSTRACT

A biologically active preparation for human or veterinary use for the selective blockade of opioid binding sites of the brain responsible for respiratory depression containing in a biologically active quantity the codeinone derivative of general formula (I) or its salt

$R^1$ means amino-, hydroxyl-, —NH-phenyl or —NH—CO—NH$_2$ groups, $R^2$ means a hydrogen atom or a hydroxyl group.

The invention also covers a process for selective blocking the opioid binding sites of the brain responsible for respiratory depression by administering to a patient in need of an analgetic a preparation containing a codeinone derivative of general formula (I) or its salt preferably three times per day in doses of 2.5–5 mg.

A preferred feature of the inventions is an analgetic composition containing a codeinone derivative of general formula (I) and in a mass ratio of 1:2–3 morphine of the formula (IV) or an other, biologically equipotent agonist type opiate or opioid compound and optionally inert, pharmaceutically acceptable accompanying materials.

3 Claims, 6 Drawing Sheets

I.

II.

$NH_2-R^3$    III.

APIOID ANALGESIC WITHOUT RESPIRATORY DEPRESSION

This is a continuation of application Ser. No. 07/934,547, filed Oct. 2, 1992, now U.S. Pat. No. 5,317,022.

The subject of the invention is a biologically active composition for selective blocking of the opiate-binding sites of the brain which are responsible for respiratory depression, which contains codeinone derivatives of the general formula (I) or its salts in a biologically active quantity.

Figure 1:
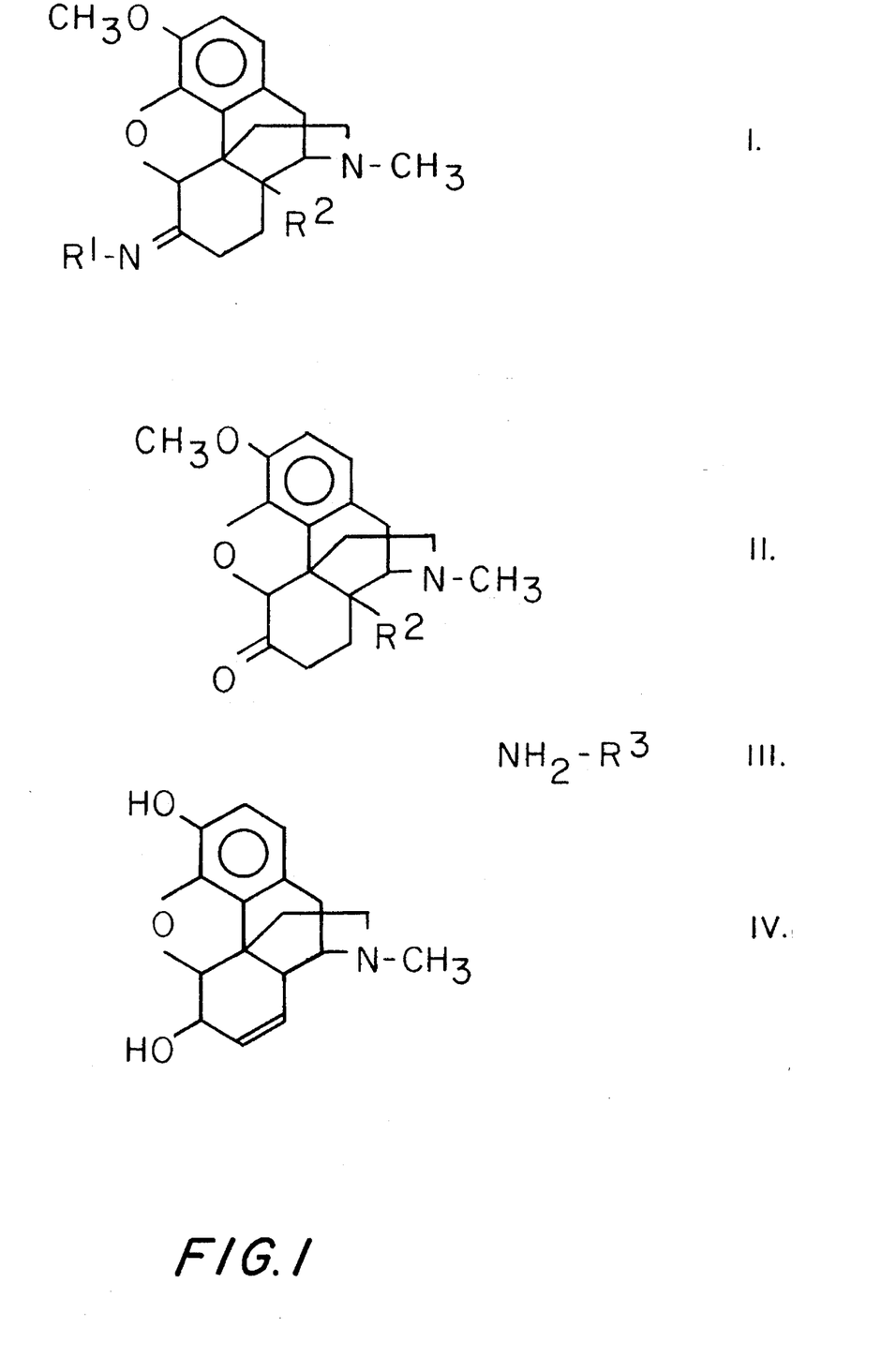
FIG. 1 sets forth structural formulas (I) compounds of the present invention, (II) a reactant for producing the compounds of formula (I), (III) a reactant for producing the compounds of formula (I), and (IV) the structural formula of morphine.
Figure 2:
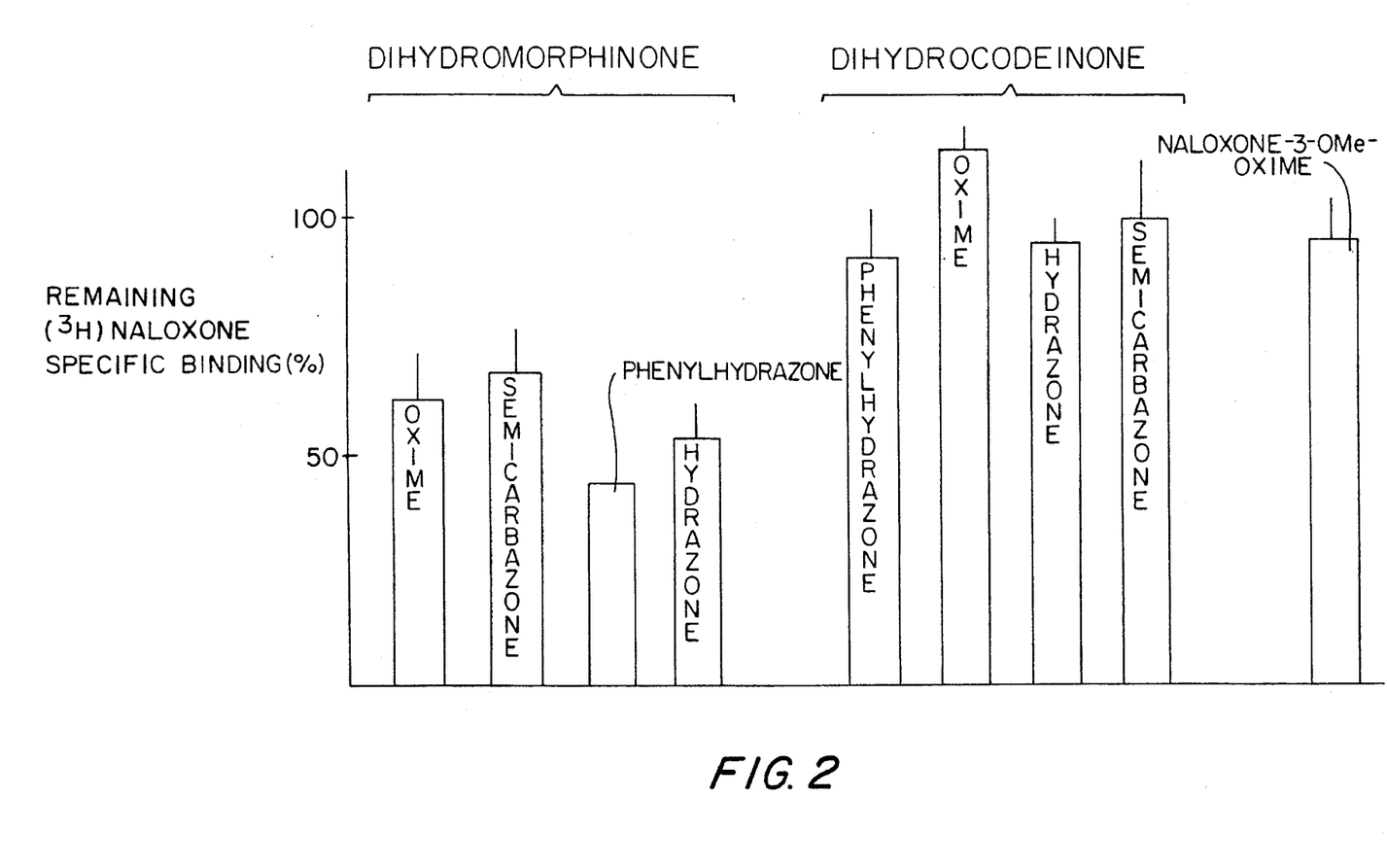
FIG. 2 is a graphical representation of specific binding of remaining $(3_H)$ naloxone of various compounds to dihydromorphinone and dihydrocodeinone.
Figure 3:
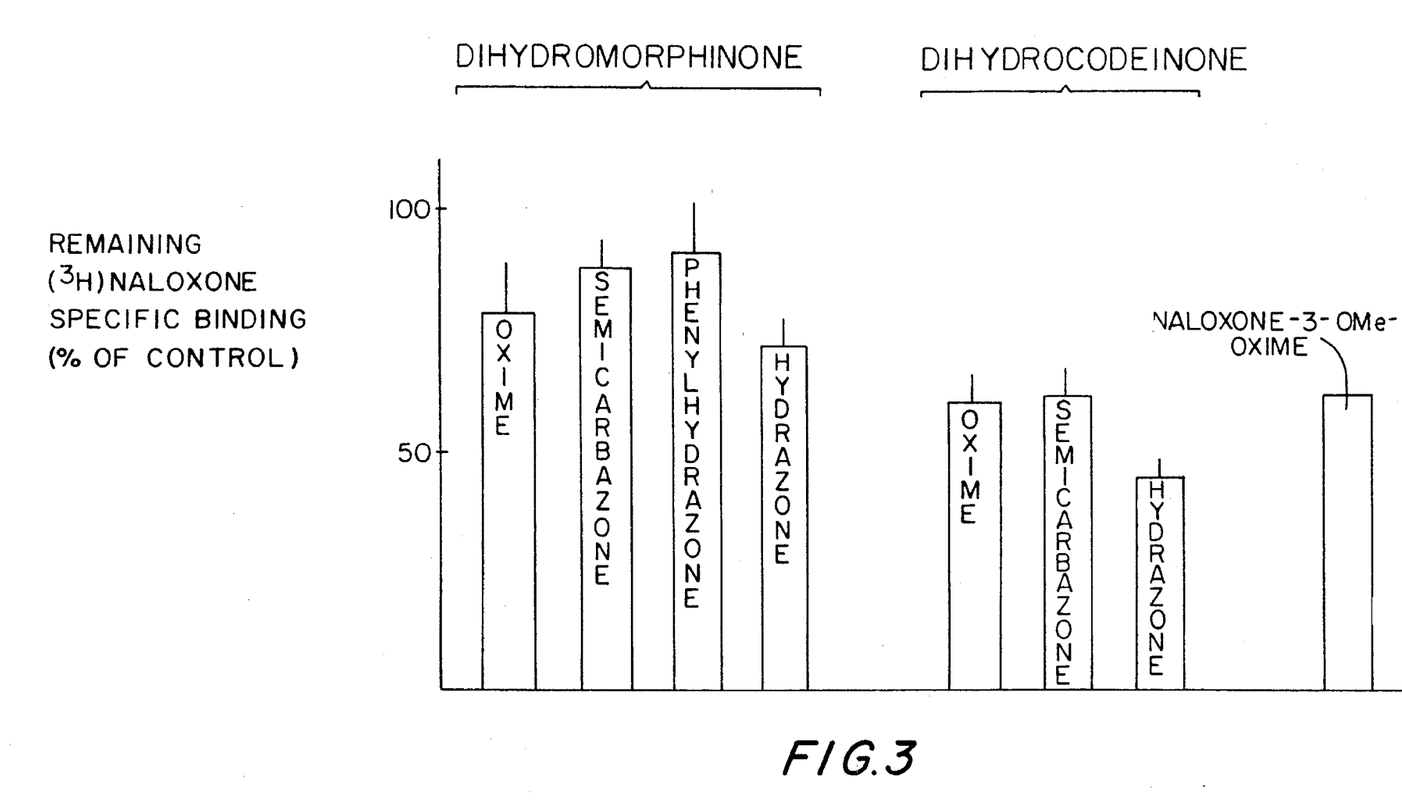
FIG. 3 is a graphical representation specific binding of remaining $(3_H)$ naloxone of various compounds to dihydromorphinone and dihydrocodeinone.
Figure 4:
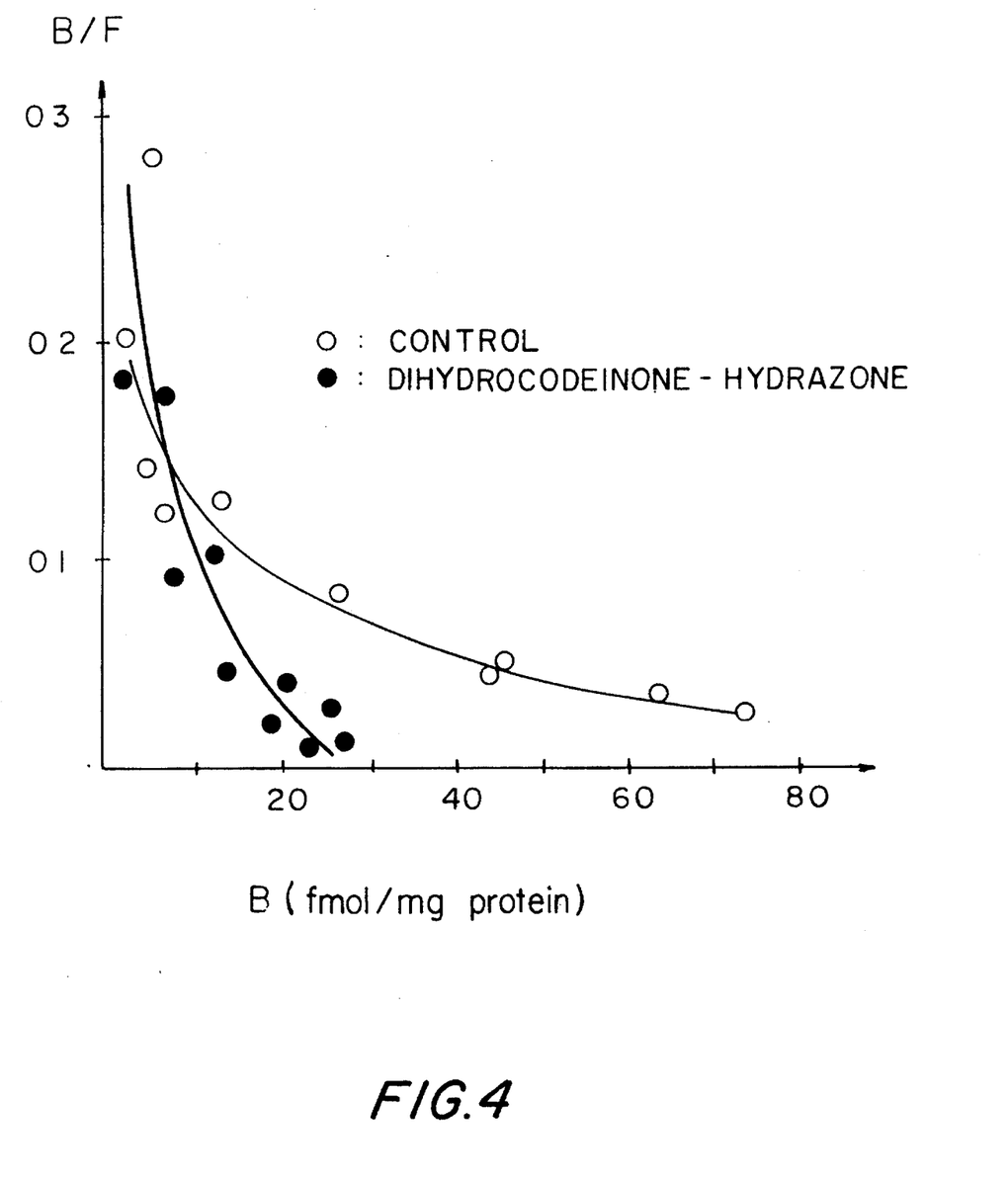
FIGS. 4, 5 and 6, are graphical representations showing the Scatchard transformations of the saturation binding isotherms of $(3_H)$ naloxone specific binding after pretreatment with dihydrocodeinone derivatives.
Figure 5:
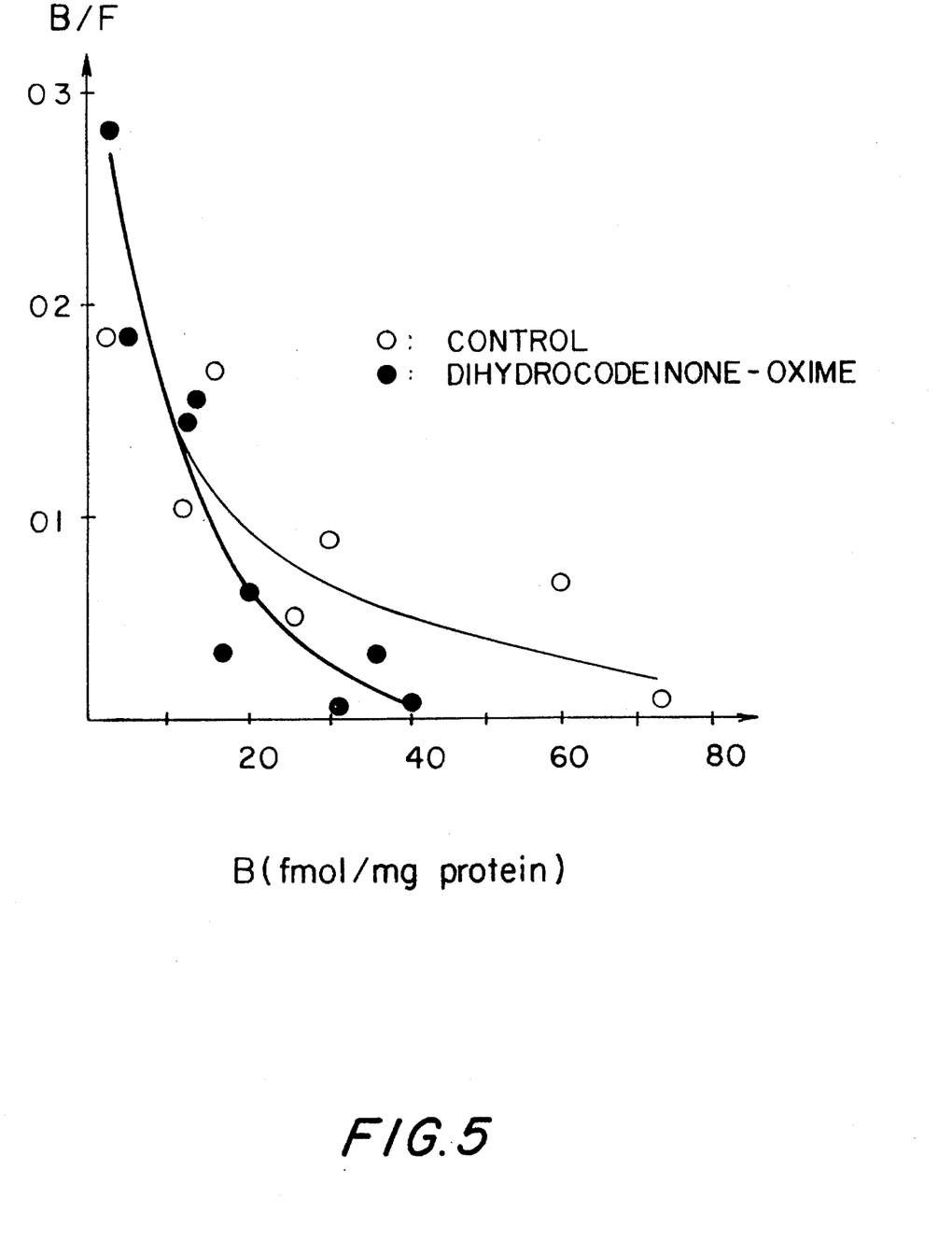
Figure 6:
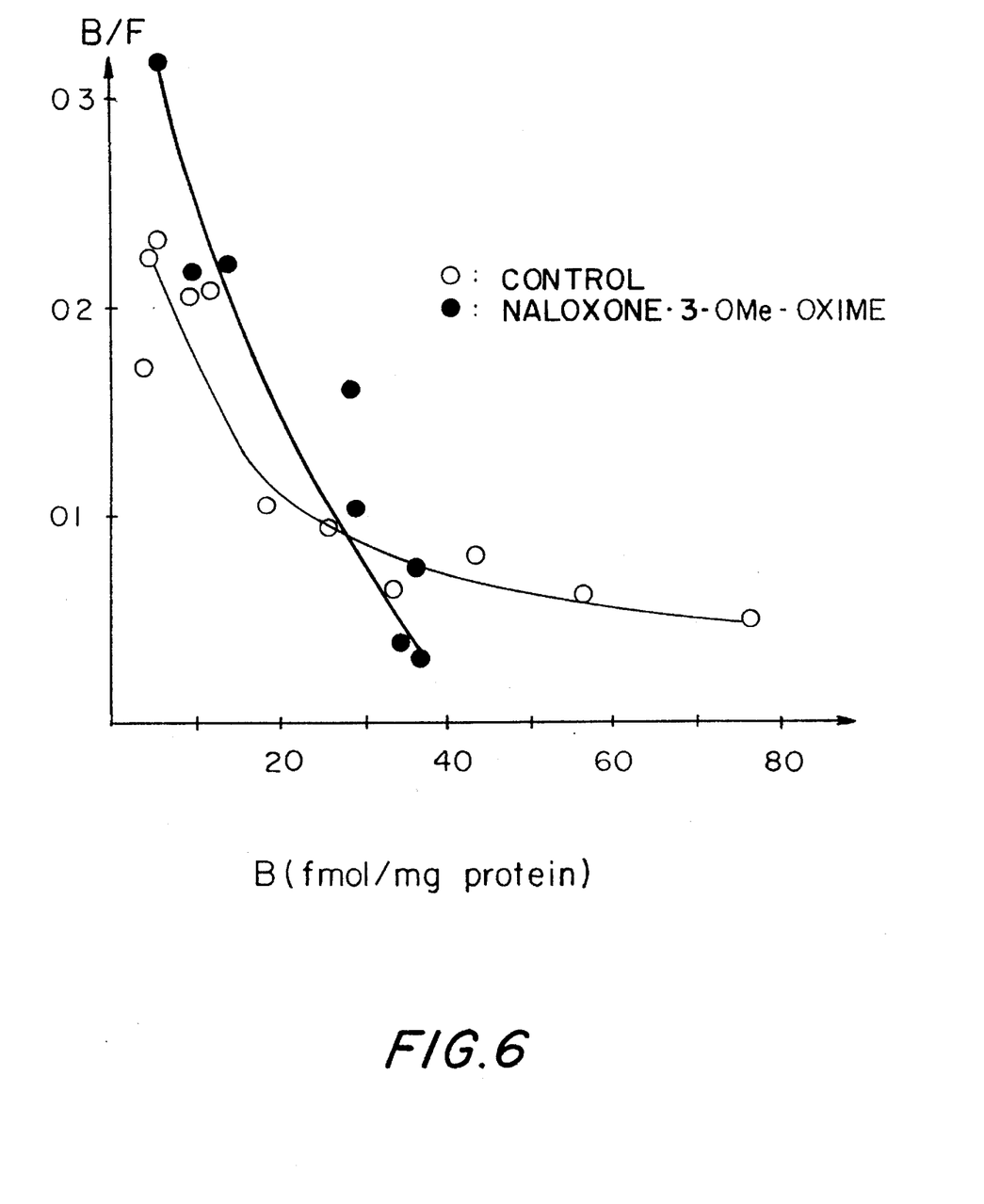

In this specification the substituents of changing signification are always the following:

$R^1$ means amino-, hydroxyl-, —NH-phenyl or —NH—CO—NH$_2$— groups, $R^2$ means a hydrogen atom or a hydroxyl group, $R^3$ means amino-, hydroxyl-, —NH-phenyl- or —NH-CONH$_2$ groups or such which can be transformed into said groups.

BACKGROUND OF THE INVENTION

It is known that the morphine-like analgetics (opiates) act as respiratory-depressants. On the course of acute toxicity investigations lethality of such compounds is attributed to this activity [Prog. Neurobiol.33(1984)1–16; 22(1984) 345].

Interpretation of relations between respiratory-depressant activity and opiate receptors is rather difficult. According to the present conceptions there are several receptors which might participate in mediating this effect. However the relative contribution of various receptor populations mediating this effect is not clear enough. Since evaluating the respiratory parameters is complicated, selectivity of the methods is questionable and because of the big differences amongst the species the difficulties are further increased. The difficulties and problems inherent in these methods partially explain the difference in receptor assignments in opioid-induced respiratory depression which have appeared in literature.

Several biochemical and pharmacological data prove the heterogeneity of the opioid receptors both in the neurological system and in the periferies [Trends. Neuro. Sci.7.(1984) 31; Pharmac. Rev.39, 197–249 (1987).]

The main receptors—marked μ, δ, . and σ receptors—show different dispersity in the different tissues, have different ligand specifities and mediate different physiological processes. In recent times it was clarified also that these main receptor types can be divided into sub-types. From these in the case of the μ type receptor it is possible to distinguish $\mu_1$ and $\mu_2$ sub-types. It is suggested that the $\mu_1$ receptor mediates the analgesic effects of opiates while the $\mu_2$ mediates opioid induced respiratory depression.

Identification of these two sub-types of opioid receptors may be brought about by way of their binding capacity to opioid receptors of so called high and low affinity. Ligands for $\mu_1$ receptors are bound to the high affinity ($^3$H)naloxone binding sites. (Their affinity constants are below nanomole concentrations.) The $\mu_2$ receptors (low affinity binding sites) mediates among others, opioid induced respiratory depression. (Their affinity constants are in the range of nanomole concentration or above.)

Ligands are known which are capable to inhibit selectively the $\mu_1$ receptors. E.g. naloxonazine, oximorphazone, several other C-6 morphinane derivatives and interestingly also some peptides (the chloro-methyl-ketones of encephalones) are of this group.

As far as we are aware no compounds capable to block the $\mu_2$ receptors were known hitherto. It is a new observation that codeinone, oxycodone and dihydrocodeinone derivatives substituted in position C-6 are bound in a partially irreversible manner to $\mu_2$ receptors.

It has to be mentioned however that the existence of $\mu_1$ and $\mu_2$ receptors has not yet found general acceptance. There were several who could not repeat the experiment which serves as main proof namely that the respiratory depression caused by morphine is not inhibited by the selective $\mu_1$ antagonist naloxonazine.

A further difficulty may be caused also by analysis of the complex action of opiates on respiration. There are opiates known which are depressing (μ-agonists: morphine etc.), others which are stimulating (receptor agonists: cyclazocine) and others which have dualistic (deprimating and stimulating) effects (partial antagonists: nalorphine).

The significance of identification of the $\mu_2$ receptor would be in theory and in practice that knowing the same there would be a possibility to synthesize such compounds which would not have respiratory depressing while having considerable analgesic properties.

It is also known that there are certain dihydro-morphinone and dihydro-codeinone derivatives substituted in position 6 with hydrazone-, phenyl hydrazone, -dinitro-phenyl-hydrazone, semicarbazone and thiosemicarbazone groups as well as their 14-OH-derivatives possess increased analgesic activity as compared with the analogues which are 6-unsubstituted (Hungarian patent application No. 56-85 or patent specification 199.901).

The C-6 carbonyl group of the morphinane ketones is easily substituted and earlier publications suggest that changes of this type in general do not influence the opioide character of the ligand.

It has been stated when investigating 6-substituted hydrazone derivatives of 14-hydroxy- dihydro-morphinone [J.Med.Chem. 23 (1980) 674–677, Pharm.Res. 3 (1986) 56–60, Life Sci., 40 (1987) 1579–1588] that both the μ and the δ high affinity binding sites are irreversibly blocked by these derivatives [J.Pharm. Exp. Ther. (1980) 214 and 455–462 ]. It has been shown by pharmacological tests that, irreversible blocking of this receptor is manifested in the case of agonists in a long-lasting analgesic effect, while in the case of antagonists the analgetic activity of morphine is blocked for a long period of time while however the protection against lethal respiratory depression does not take place. [Life Sci. 31 (1983) 1389–1392, Science 208 (1989) 514–516]. It has thus been stated that the opiate analgesia is mediated by the common receptor named $\mu_1$. Thus it would be a most desirable task for pharmaceutical planning to separate the analgetic effect from other opiate effects.

SUMMARY OF THE INVENTION

When starting work according to our invention we studied different C-6 substituted. (hydrazone-, phenylhydrazone-, di-nitro-phenylhydrazone-, oxime-, semicarbazone-) derivatives of dihydro-morphinone and dihydro-codeinone on brain membranes of rats. The C-6 substitution did not change their affinities to ($^3$H)naloxone-binding sites in the case of substituents of small size, while the affinity decreased in case of substituents having a greater volume.

We stated that all tested C-6 substituted derivatives of oxymorphone and dihydromorphinone are blocking irreversibly, in a dose-dependent manner the specific bondage of (³H)naloxone at isotope concentrations of 1 nM and this concerns the μ₁ receptor.

DESCRIPTION OF PREFERRED EMBODIMENTS

We have found surprisingly that oxycodone and dihydrocodeinone derivatives of general formula (I) are irreversible inhibitors in a dose-dependent manner of specific binding of (³H)naloxone at isotope concentrations of 1 nM and they have a lower affinity to the (³H)naloxone binding sites as compared with the corresponding morphine derivatives.

We ascertained however that at isotope concentrations of 10 nM preincubation with these dihydrocodeinone derivatives blocks the specific binding of (³H)naloxone irreversibly and completely, as well seen from saturation isotherms of (³H)naloxone (preincubation of the membranes with these dihydrocodeinone derivatives followed by washing). It essential that this involves the binding site of low affinity (μ₂) which is responsible for respiratory depression.

In our pharmacological tests based on the above we searched the reply whether the derivatives of general formula (I) would be exempt from respiratory depression actions which are presumably mediated by the μ₂ receptor. Starting from the fact that toxicity of morphine is attributed to respiratory paralysis, we conducted toxicity tests of the above compounds and morphine on rats to get indirect information on the nature of-the respiratory depressant activity. From the classical opiate spectrum we investigated along with the analgetic effect the sedative action as well.

We verified that the codeinone derivatives of general formula (I) significantly inhibit the lethal respiratory depression caused by morphine (e.g. on rats), when increasing the LD₅₀ value measured on morphine controls in the average to its twofold.

On the basis of the tables shown in the experimental examples we also can state that a part of the compounds stimulated in small dose ranges tile frequency of respiration and some even the amplitude, administered i.v. and s.c. For example the oxycodone-semicarbazone and -oxime when used in small doses considerably increase the respiration number and in some tests they reduced the depressant effect of morphine. In all experiments we reversed respiration with naloxone to prove that the depression was mediated by an opiate receptor. When administering together the morphine effect was slightly inhibited in a 100 μg/kg dose. Oxycodone hydrazone increases both the volume and the frequency of respiration in an 50 μg/kg dose. When administered after morphine a partial reversal takes place. While somewhat depressing respiration oxycodone-phenyl-hydrazone partially antagonizes the effect of morphine. It has to be mentioned that amongst the referred "mother compounds" dihydrocodeinone and oxycodone cause respiratory depression in 50–2500 μg/kg and 10–2500 μ/kg s.c. doses. Both compounds unambiguously potentiate the respiratory depression effect of morphine.

The above experiments suggest that the codeinone derivatives of general formula (I) according to our invention block selectively the opioid binding sites of the brain which are mediating respiratory depression and thus they can be used both in human and in veterinary preparations in all cases where such blocking is necessary.

Thus the codeinone derivatives of general formula (I) can be used as active ingredients in analgetic preparations without the appearance of lethal respiratory depression after longer treatment or higher doses.

The derivatives of general formula (I) also can be used preferably in combinations according to our invention. Thus it is specifically important to our view that when administered together with morphine the respiratory depression can be decreased and the lethal effect can be avoided. Thus it is possible to administer morphine in prolonged and higher doses in cases where the patient needs it without the occurrence of lethal respiratory paralysis.

In preparations where morphine and the codeinones of general formula (I) are applied together the mass proportion or morphine:codeinone derivative amounts to 1:2–3.

Instead of morphine biologically equipotent amounts of other opiates of the agonist type or opioid compounds can be used in these combination preparations. Such compounds are e.g. morphinanes, benzomorphanes, opioid peptides or other pentacyclic compounds with morphine activity.

In addition to the above active ingredients the compositions according to our invention contain inert, pharmaceutically acceptable additive compounds.

A further subject of our invention consists in a method to selectively block opioid binding sites of the brain which are responsible for depression of respiration by way of administering to the patient in need of such treatment a composition containing a codeinone derivative of general formula (I) or its salt preferably in a 3×2,5–5 mg daily dose.

It is preferable to use the product in the form of i.m., i.v., or epidural injections it is however possible to use other dosage forms as well.

A further subject of our invention is a process for the preparation of a biologically active composition containing codeinone derivatives of general formula (I) by reacting a ketone of the general formula (II) with a hydrazine derivative of the formula (III) by admixing kodeinone derivatives of the general formula (I)—[alone or applied together with 1:2–3 mass ratio of morphine or some other opiate or opioid compound of the agonist type]—with additive or auxiliary compounds usually applied in pharmaceutical production for human or veterinary purposes so as to formulate compositions capable to block the opioid binding sites responsible for respiratory depression, preferably analgesics.

According to our invention the codeinone derivative of general formula (I) can be present in tile form of its salt formed with mineral or organic acids preferably phosphoric acid, hydrochloric acid.

According to our invention it is possible to use the compounds in the form of their cis and/or trans isomers.

We have thus stated—as compared with the molecules protected in our Hungarian Patent No. 199.901 —that according to our invention it is only possible to use a distinct, limited part of the 6-substituted derivatives protected there.

It is not possible to use the big group of morphinane derivatives. Thus the selective binding exposed according to our invention represents a property, the recognition of which constitutes the essential basis of our invention and on the basis of this new point of view the selection of outstandingly useful compounds out of the bigger range of others.

According to our knowledge the oximes falling under general formula (I) have never been described as pharmaceuticals at all.

The details of our invention are illustrated in the Examples.

I. EXAMPLES FOR COMPOSITIONS

Compositions containing the following active ingredients are prepared with usual additive material and methods:

TABLE

| Compound | | tablet or capsule | im. or sc. inj. | iv. inj. | epidur. inj. |
|---|---|---|---|---|---|
| I.1. | Oxycodone-oxime phosphate | 5 | 2 | 1 | 0,5 |
| I.2. | Oxycodone-oxime .HCl + morphine.HCl | 2 5,0 | 0,5 5,0 | 0,1 5,0 | 0,1 1,0 |
| I.3. | Oxycodone-semicarbazone-bi-tartarate | 2,5 | 1 | 0,5 | 0,1 |
| I.4. | Oxycodone-phenylhydrazone.HCl | 2,5 | 1 | 0,5 | 0,1 |
| I.5. | Oxycodone-hydrazone.HBr | 2,5 | 1 | 0,5 | 0,1 |
| I.6. | Oxycodone-semicarbazone.HCl + morphine.HCl | 2,5 5,0 | 1 5,0 | 0,5 5,0 | 0,1 1,0 |
| I.7. | Oxycodone-phenyl hydrazone.HCl + morphine.HCl | 2,5 5,0 | 1 5,0 | 0,6 5,0 | 0,1 1,0 |
| I.8. | Oxycodone-hydrazone.HCl + morphine.HCl | 2,5 5,0 | 1 5,0 | 0,5 5,0 | 0,1 1,0 |
| I.9. | Dihydrocodeinone-oxime phosphate | 10,0 | 5,0 | 2,0 | 1,0 |
| I.10. | Dihydrocodeinone-oxime.HCl + morphine.HCl | 5 5,0 | 2,5 5,0 | 1 5,0 | 0,1 1,0 |

The dose of the active ingredient is given in relation to the base, the size is mg/formulated unit (tablet, ampoule).

Example I.11.

Tablets of the following composition are prepared with usual methods:

| | |
|---|---|
| Salt of the active ingredient | 5,0 mg (calculated as base) |
| Lactose | 60.0 mg |
| Starch | 30.0 mg |
| Magnesium stearate | 1,0 mg |
| Talc | 3,0 mg |

II. BINDING TESTS

Methods

Membrane preparation: A crude membrane fraction from rat brain (PVG/C strain) was prepared [Mol.Pharm.11 (1975) 340–351] and the protein content was defined [Anal. Biochem. 72 (1976) 248–254).

Description of the Binding Essay

The membrane suspension (200–400 μg protein) was incubated with the specific radioligand for 1 hour on ice. Incubations were terminated by rapid filtration under vacuo followed by washing with ice-cold tris-HCl buffer (50 mM, pH 7,4). Radioactivity was measured in a toluene-based scintillation mixture on a LKB Minibeta Liquid Scintillation Spectrophotometer. Nonspecific binding was defined in the presence of 10 μM unlabeled naloxone. All assays were performed in triplicate and repeated several times. $K_i$ values were determined from equilibrium experiments and calculated with the Tshang-Prusov equation. The data were evaluated using the Ligand program [Anal.Biol. Chem. 107 (1980) 220–239] (Data shown on Table III/1).

Determination of Wash-resistant Binding

After preincubation a thorough washing was performed. [Life Sci. 32 (1983) 2777–2784]. Control values are represented by the specific binding of ($^3$H)naloxone to membranes preincubated with a buffer and treated in the same way. Heterologous displacement experiments were used to evaluate the affinity of the investigated compounds for ($^3$H)naloxone binding sites. Results are shown in Table 11/2.

II.1. BINDING TEST

TABLE II/1

Affinity constants ($K_i$nM) of different opioid ligands in competition assays

| | hydrazone | phenyl-hydrazone | semi carbazone | oxime | salt |
|---|---|---|---|---|---|
| oxymorphone | 2 | 20 | 4 | 2 | sulfate |
| dihydromorphinone | 6 | 5 | 3 | 2 | sulfate |
| oxycodone | 800 | 1150 | 588 | 32 | HCl |
| dihydrocodeinone | — | 323 | — | 52 | HCl | membranes were incubated with ($^3$H)naloxone (1nM) and with increasing concentrations of the ligands.

Evaluation

The oxime derivatives exhibit the highest affinity for ($^3$H)naloxone binding sites. The codeinone and dihydrocodeinone derivatives have substantially higher $K_i$ values,

II.2. ESSAY ON WASH-RESISTANT BINDING

TABLE II/2

Affinity constants of oxycodone and dihydrocodeinone derivatives

| Example | Compound.HCl | $K_i$(nM) |
|---|---|---|
| IV.2. | Oxycodone | 127 |
| IV.3. | Oxycodone-oxime | 32 |
| IV.5. | Oxycodone-semicarbazone | 588 |
| IV.8. | Oxycodone-phenylhydrazone | 1150 |
| | Dihydrocodeinone | 476 |
| IV.1. | Dihydrocodeinone-oxime | 53 |
| | Dihydrocodeinone-phenylhydrazone | 323 |

The membranes were preincubated with ($^3$H)naloxone (1 nM) and with increasing concentrations of tested compounds and the specific binding of the remaining ($^3$H)naloxone was measured after several washings. The data given represent the average of 2–4 data observed.

The codeinone derivatives were measured in 10 μM preincubation concentrations. Evaluation: Table V. shows that the compounds of general formula (I) are week, irreversible inhibitors of specific binding of ($^3$H)naloxone at 1 nM concentration, especially on high activity receptors. At higher concentrations the situation is reversed and they inhibit mainly the low affinity receptors.

As it is seen in Figure VI. the remaining ($^3$H)naloxone specific binding is significantly decreased at 10 nM isotope concentration as a result of preincubation with dihydrocodeinone-derivatives, while this decrease is rather small if preincubation takes place with dihydro-morphinone derivatives.

It was already shown previously [Life Sci.40 (1980) 1579–1588, J.Pharm. Exp. Ther.214 (1980) 455–462] that preincubation with hydrazone derivatives of oxymorphone and naloxone irreversibly inhibits the high affinity (3H)naloxone component, whereby the low affinity component remains unchanged. As seen on Table II/1., the oxycodone and dihydro-oxycodone derivatives show a lower affinity to the ($^3$H)naoxone binding sites as compared with the correspondent morphine derivatives, if the isotope concentration is low.

These ligands however strongly inhibit at higher (10 nM) concentrations the ($^3$H)naloxone specific binding. This is why we studied the effect of preincubation with these derivatives on saturation isotherms of ($^3$H)naloxone.

Figure VII. shows the Scatchard transformations of the saturation binding isotherms of ($^3$H)naloxone specific binding after pretreatment with dihydrocodeinone derivatives and with buffer only as a control, From the Scatchard analysis the result is clearly seen, that after preincubation and intensive washings the low affinity receptor-effect almost completely disappears.

III. PHARMACOLOGICAL TESTS

It is characteristic for the compounds that their greater part shows a substantial and some a light agonist (analgetic or sedative) effect (Tables No. 1,2,3).

III.1. ANALGETIC EFFECTS

Comparison on the basis of data obtained in 4 tests on rats and mice ($ED_{50}$ mg/kg):

TABLE III/1

| compound | hot plate (rat) | tail flick (rat) | writhing test (mice) | algolyt. test (rat) 100% activity |
|---|---|---|---|---|
| Oxycodone-oxime .phosphate | 1,8 | 1,0 | 0,11 | 10,0* |
| Oxycodone-semi-carbazone.bi-tartarate | 0,58 | 0,35 | 0,15 | 5,0* |
| Oxycodone-phenyl-hydrazone.HCl | 0,8 | 1,2 | 1,2 | 10,0* |
| Oxycodon-hydrazone.HBr | 0,46 | 0,65 | 0,35 | 10,0* |
| Oxycodone-thio-semicarbazone .HCl | 8,5 | 4,5 | — | 100,0 |

TABLE III/1-continued

| compound | hot plate (rat) | tail flick (rat) | writhing test (mice) | algolyt. test (rat) 100% activity |
|---|---|---|---|---|
| Dihydrocodei-none-semicarbazone.HCl | 0,38 | 0,35 | — | 10,0* |
| Dihydrocodei-none phenyl-hydrazone.HCl | 2,4 | 2,3 | — | 10,1** |
| Dihydrocodei-none-oxime .phosphate | 4,2 | 3,7 | 0,38 | 25,0* |
| Dihydrocodeinone thio_semicarbazone.HCl | 1,7 | 0,6 | — | 5,0 |
| Morphine | 3,6 | 1,8 | 0,45 | 15,0 |
| Oxycodone | 0.92 | 0,68 | 0,45 | 2,2 |
| Dihydrocodeinone | 2,2 | 0,98 | 0,9 | 4,9 |

*catalepsy
**convulsion

Methods

Eur.J.of Pharm. (1982)239–241; Arzn.Forschung 38 (1938) 552. The strongest analgetic on the hot plate test is the dihydrocodeinone-semicarbazone ($ED_{50}$:0.38 mg/kg hot plate, tail flick). On the algolytic test the oxycodone-oxime, -semicarbazone, -phenylhydrazone and -hydrazone are capable to total assuage of pain—though amidst the symptoms of slight cathatony—practically in the order of magnitude of morphine or the mother compounds (oxycodone, dihydrocodeinone).

III.2. TESTING ON SEDATIVE ACTIVITY

Inactine (35 mg/kg) was used as a base narcotic.

TABLE III/2

Sedative (narcosis potentiating effect ($ED_{500}$ % mg/kg) s.c. on rats

| Name | $ED_{500}$ % mg/kg* |
|---|---|
| oxycodone-hydrazone.HBr | 0,45 |
| oxycodone oxime.phosphate | 0,5 |
| oxycodone-semicarbazone.HCl | 1,5 |
| oxycodone-phenylhydrazone.HCl | 1,5 |
| dihydrocodeinone-phenylhydrazone.HCl | 3,5 |
| dihydrocodeinone-semicarbazone .bitartarate | 1,0 |
| morphine | 1,75 |
| dihydrocodeinone | 1,9 |
| oxycodone | 1,2 |

*$ED_{500}$% = dose increasing narcosis to five times the control.
The doses of the active ingredients are always given in relation to the base.

Evaluation

All investigated compounds potentiate the activity of Inactine strongly. The duration of narcosis is most effectively prolongated by oxycodone-hydrazone and -oxime respectively.

III.3. INVESTIGATION OF PHYSICAL DEPENDENCY

TABLE III/3

"jumping test" on mice

| name | treatment 7 xmg/kg ip. | naloxone 50 mg/kg ip. | number of jumps /mouse (average) | % relation of jumping animals |
|---|---|---|---|---|
| morphine | 100 | + | 34,5 | 100 |
| oxycodone-oxime.phosphate | 2 | + | 2,7 | 70 |
| | 5 | + | 2,5 | 50 |
| oxycodone-hydrazone.HBr | 1 | + | 1,5 | 50 |

The dose of the active ingredient is given related to the base.

Table III/3. shows the results of an informative physical dependency study on the jumping test on mice. The mice were treated for three days with a total of 7 times i.p. with a high dose of the compounds to be tested and after the final injection the symptoms off withdrawal are generated by administration of a morphine antagonist, i.e. a constraint for jumping is provoked. Morphine-equivalent quantities were administered from the test compounds. In the case of morphine the dose which effects dependence with certainty amounts to 7×100 mg/kg. Within this group on administration of 50 mg/kg off naloxone the average jumping rate amounted to 34,5 (total jumping number/jumping animals) and 100% off the investigated animals did jump. Oxycodone-semicarbazone-oxime and -hydrazone respectively when administered in equi-analgetic doses did not result but in a very low, almost negligible number of jumping reactions while 50–70% were participating. The capacity of dependence of these compounds is thus unusually low.

III.4. MORPHINE TOXICITY TESTS

Morphine and the test substances were administered together, s.c, to rats. As seen from Table III/4. almost twice as much is needed from morphine to develop the same mortality meaning that toxicity of morphine is decreased to almost its half as a result of the activity of effective test substances (oxycodone-oxime, -semicarbazone, -phenylhydra-zone, -hydrazone and dihydrocodeinone-oxime). Dihydrocodeinone-semicarbazone and -phenyl-hydrazone are less active. Oxycodone and dihydrocodeinone potentiate toxicity of morphine (!).

TABLE III/4

Change of morphine toxicity in the presence of test substances (on rats)

| Name | Dose mg/kg s.c. | Morphine LD$_{50}$ g mg/kg s.c. | Combination LD$_{50}$/ morphine LD$_{50}$ |
|---|---|---|---|
| Oxycodone-oxime.phosphate | 15 | 620 | 2,2 |
| Oxycodone-semicarbazone.bitartarate | 50 | 580 | 2,0 |
| Oxycodone hydrazone.HBr | 10 | 650 | 2,3 |
| Dihydrocodeinone-phenyl-hydrazone.HCl | 50 | 500 | 1,7 |
| Dihydrocodeinone oxime.phosphate | 25 | 750 | 2,6 |
| Oxycodone | 10 | 160 | 0,57 |
| Dihydrocodeinone | 10 | 150 | 0,53 |
| Morphine | — | 280 | 1,0 |

The doses of the active substances are given in relation to the base.

III.5. EFFECT ON RESPIRATION TEST ON RABBITS

Method

Investigation was carried out on conscious rabbits of both sexes and of 3–4 kg weight by way of a Marey-drum. Frequency and amplitude of respiration were quantitatively evaluated.

Morphine decreased both frequency and volume of respiration in 2,5–5 mg/kg doses. Some results are shown in Table III/5.

TABLE III/5

Effects on respiration on conscious rabbits

| Compound | dose µg/mg s.c. | respiration volume frequency/ min. | | respiration effect |
|---|---|---|---|---|
| Morphine.HCl | 2500–5000 i.v., s.c. | ‖ | ‖ | depression |
| Dihydrocodeinone.HCl | 10–5500 i.v., s.c. | ǀ | ǀ | depression |
| Oxycodone.HCl | 10–2500 i.v., s.c. | ǀ | ǀ | depression |
| Oxycodone-semicarbazone.HCl | 100–500 + morphine* | ‖ | ǀ | morphine-inhibition |
| Oxycodone-hydrazone.HCl | 50 50 (administered after morphine* | ǀ | ǀ | slight reversion |
| Oxycodone-phenylhydrazone.HCl | 100–5000 1000 | 0 ǀ | 0 ǀ | no change slight stym. |

*Morphine dose in combinations amounts to 5 mg/kg.

III.6. EFFECT ON RESPIRATION TEST ON CONSCIOUS RABBITS

Method

The method as described above in Example III.5 was used on conscious rabbits of 2,5–3 kg weight. Registration was continued for 3–4 hours. The samples were injected under the skin of the neck and the respiration parameters were registered at intervals of 1.0 minutes.

Type A test: Determination of the dose-effect diagram of the substances ("low dose region" and "high dose region") between 0.01 to 2.5 mg/kg alone and after selection of particular dose values investigation off morphine prevention.

Type B test: Sequence of application was the following: 5 mg/kg morphine were administered (causing with certainty respiratory depression) and after 10–20 minutes it was investigated whether the depression could be reversed.

Type C test: Administration of 5 mg/kg of morphine and the investigated substance together to clarify whether the substance is capable to reduce the effect of morphine.

Some of the results are shown in the following tables.

TABLE III/6

| Oxycodone oxime (OX) | | | | | |
|---|---|---|---|---|---|
| OX dose mg/kg | pretr. period | morphine mg/kg | pretr. period | resp.change | |
| s.c. | min. | s.c. | min. | fr/min | ampl. |
| 0.005 | 30 | — | — | +30 | +30 |
| 0.1 | 30 | — | — | +47 | +40 |
| 0.025 | 30 | — | — | +28 | 0 |
| 0.5 | 10 | — | — | −50 | −50 |
| + naloxone | | | | | |
| 0.25 | 10 | — | — | +50 | +50 |
| — | — | 0.5 | 30 | −15 | 0 |
| — | — | 1.0 | 30 | −20 | 0 |
| — | — | 2.5 | 30 | −39 | −20 |
| — | — | 5.0 | 30 | −47 | −80 |
| | | | 120 | −66 | −80 |
| A. | | | | | |
| 0.1 | 10 | — | — | +57 | +20 |
| | +5 | | 30 | +71 | 0 |
| | | | 40 | −29 | −40 | pret = duration of pretreatment

TABLE III/7

| Oxycodone semicarbazone (OS) | | | | | |
|---|---|---|---|---|---|
| OS dose mg/kg | pretr. period | morphine mg/kg | pretr. period | resp.change | |
| s.c. | min. | s.c. | min. | fr/min | ampl. |
| 0.01 | 10 | — | — | +48 | 0 |
| | 30 | — | — | +51 | +20 |
| 0.025 | 30 | — | — | +51 | +20 |
| 0.05 | 10 | — | — | +50 | +75 |
| 0.025 | 10 | — | — | +48 | +20 |
| | 20 | 5 | 20 | +24 | −16 |
| | 30 | | 30 | +13 | −20 |
| 0.50 | 10 | — | — | +36 | 0 |
| | 30 | 20 | 20 | +10 | 0 |

TABLE III/8

| Oxycodone phenylhydrazone (OP) | | | | | |
|---|---|---|---|---|---|
| OP dose mg/kg | pretr. period | morphine mg/kg | pretr. period | resp.change | |
| s.c. | min. | s.c. | min. | fr/min | ampl. |
| A. | | | | | |
| 0.1 | 10 | — | — | +33 | +20 |
| 0.5 | 10 | — | — | +16 | 0 |
| | | 5 | 10 | −17 | −20 |
| | 60 | | | 0 | 0 |
| B. | | | | | |
| — | — | 5 | 10 | −40 | −40 |
| 1.0 | | | 20 | −16 | +15 |
| | | | 30 | −6 | +20 |
| C. | | | | | |
| 0.25 | | 5 | 20 | +44 | +20 |
| | | | 30 | +92 | +30 |
| 0.25 | | 10 | 10 | +23 | +20 |

TABLE III/8-continued

| Oxycodone phenylhydrazone (OP) | | | | | |
|---|---|---|---|---|---|
| OP dose mg/kg | pretr. period | morphine mg/kg | pretr. period | resp.change | |
| s.c. | min. | s.c. | min. | fr/min | ampl. |
| 0.25 | | 20 | 30 | −8 | 0 |

TABLE III/9

| Oxycodone hydrazone (OH) | | | | | |
|---|---|---|---|---|---|
| OH dose mg/kg | pretr. period | morphine mg/kg | pretr. period | resp.change | |
| s.c. | min. | s.c. | min. | fr/min | ampl. |
| A. | | | | | |
| 0.25 | 20 | — | | +150 | +20 |
| | 30 | — | | +127 | +20 |
| | | 5 | 10 | −36 | −30 |
| C. | | | | | |
| 0.25 | | 5 | 20 | +30 | +10 |

TABLE III/10

| Dihydrocodeinone-phenylhydrazone (DP) | | | | | |
|---|---|---|---|---|---|
| DP dose mg/kg | pretr. period | morphine mg/kg | pretr. period | resp.change | |
| s.c. | min. | s.c. | min. | fr/min | ampl. |
| A. | | | | | |
| 0.01 | 10' | — | — | +85 | 0 |
| | 20' | — | — | +96 | 0 |
| 0.025 | 10' | — | — | +114 | 0 |
| | 20' | — | — | +114 | 0 |
| 0.05 | 10' | — | — | +132 | 0 |
| C. | | | | | |
| 0.25 | together | 5 | 10' | +39 | 0 |
| | | | 20' | +19 | 0 |
| | | | 30' | −3 | 0 |
| | | | 50' | −4 | 0 |

The Table shows that doses of 0.01 to 0.05 mg/kg considerably increase the frequency without influence on the amplitude of respiration. Doses of 0.25 mg/kg where administered together with morphine retard depression to some degree.

IV. CHEMICAL PROCESS EXAMPLES (Method: Hungarian Patent Specification No. 199.901)

IV.1. Dihydrocodeinon-oxime 1,5 g of hydroxylamine-chlorohydrate are reacted in 70 ml of water with 3,0 g of dihydrocodeinone base for 3 hours and then adjusted to pH=9–10. The oxime precipitates as crystals, which are filtered, washed with water and crystallized from propanol. The product amounts to 2,5 g. M.p.: 265°–266° C.

IV.2. 14-Hydroxy-dihydrocodeinone-oxime

The product of Example IV.1. is crystallized from aqueous ethanol. M.p.: 194° C.

IV.3. 14-OH-dihydrocodeinone-hydrazone (trans)

5 ml of 100% hydrazone hydrate are heated with 2,0 g of 14-OH-dihydrocodeinone in 10 ml of dimethyl-formamide for two hours and then poured into water. The crystalline product which precipitates is isoiated and chromathographized on silicagel (chloroform-methanol 9:1,v/v). The pure fractions obtained by TLC eluating with the eluent chloroform: methanol: cc. ammonium hydroxide mixture 90:10:5 are crystallized from methanol. M.p.:192°–194° C.

IV.4. 14-OH-Codeinone-hydrazone

Using the method of Example IV.3. 1,8 g 14-OH-codeinone-hydrazone are obtained from 2,0 g of 14-OH-codeinone. The crude product contains two components as shown by TLC using the eluant chloroform: methanol: cc.ammonium hydroxide 90:10:5. The main component can be obtained in pure state by way of preparative thin-layer chromatography. Crystallized from ethanol m.p.: 212°–215° C.

IV.5. 14-OH-dihydrocodeinone-semicarbazone (trans)

According to the method described in Example IV.4. 3,2 g of the crude product are obtained from 3,0 g of 14-OH-dihydrocodeinone, which is the mixture of syn and anti isomers (cis:trans=1:1). By way of crystallization (chloroform-ethanol) the pure trans semicarbazone is obtained. M.p.: 236°–238° C.

IV.6. 14-OH-dihydrocodeinone-phenylhydrazone (cis)

Starting from 1,55 g of 14-OH-dihydrocodeinone 1,7 g of 14-OH-dihydrocodeinone-phenylhydrazone are obtained with the process given in Example IV,3. M.p. after recrystallization: 174°–176° C. Pure cis isomer.

We claim:

1. Method of achieving opioid analgesia while inhibiting respiratory depression, comprising administering to a patient requiring the same an analgesic effective amount of a compound of the formula I:

wherein $R^1$ is $-NH_2$, $-NC_6H_5$ or $-CO-NH_2$, and $R_2$ is H or OH, or a pharmaceutical acceptable salt thereof, said analgesic effective amount acting also to inhibit respiratory depression.

2. Method according to claim 1, wherein said compound or salt is administered about 3 times a day in doses of about 2.5–5 mg.

3. Method according to claim 2, wherein said compound or salt is administered along with an additional opioid agonist, which additional. opioid against causes respiratory depression, and said compound of Formula I inhibiting the respiratory depression effect of said opioid agonist and said additional opioid agonist is used together with said compound of Formula I or its salt in a molar ratio of about 1:2–3.

* * * * *

UNITED STATES PATENT AND TRADEMARK OFFICE
CERTIFICATE OF CORRECTION

PATENT NO.  : 5,457,110
DATED       : October 10, 1995
INVENTOR(S) : Anna Borsodi, Zsuzsa Fürst, Sándor Hosztafi, Schäfferné E. Varga, Beáťa Buzás, Tamás Friedmann, Sandor Benyhe and Mária Szücs It is certified that error appears in the above-indentified patent and that said Letters Patent is hereby corrected as shown below:

On the Title page, item [54], in the Title;

Delete "APIOD" and insert therefor, — OPIOID —.

Signed and Sealed this

Twentieth Day of February, 1996

Attest:

BRUCE LEHMAN

*Attesting Officer*    Commissioner of Patents and Trademarks